(12) United States Patent
Lin

(10) Patent No.: US 6,458,133 B1
(45) Date of Patent: Oct. 1, 2002

(54) SPINAL FIXATION AND RETRIEVAL DEVICE

(76) Inventor: Chih-I Lin, 14292 Spring Vista La., Chino Hills, CA (US) 91709

( * ) Notice: Subject to any disclaimer, the term of this patent is extended or adjusted under 35 U.S.C. 154(b) by 0 days.

(21) Appl. No.: 09/765,641

(22) Filed: Jan. 22, 2001

(30) Foreign Application Priority Data

Dec. 19, 2000 (TW) ........................................ 89222042 U

(51) Int. Cl.⁷ .............................................. A61B 17/56
(52) U.S. Cl. ............................. 606/69; 606/71; 606/72; 606/65
(58) Field of Search ............................. 606/69, 70, 71, 606/61, 65, 72; 623/11.11, 16.11, 17.11, 17.16

(56) References Cited

U.S. PATENT DOCUMENTS

| | | | | |
|---|---|---|---|---|
| 5,569,251 A | * | 10/1996 | Baker et al. ................... | 606/69 |
| 5,578,034 A | * | 11/1996 | Estes ............................. | 606/61 |
| 6,193,721 B1 | * | 2/2001 | Michelson ..................... | 606/70 |
| 6,224,602 B1 | * | 5/2001 | Hayes ........................... | 606/69 |
| 6,235,034 B1 | * | 5/2001 | Bray ............................. | 606/71 |
| 6,241,731 B1 | * | 6/2001 | Fiz ................................ | 606/69 |

* cited by examiner

Primary Examiner—Pedro Philogene
(74) Attorney, Agent, or Firm—Bacon & Thomas

(57) ABSTRACT

A spinal fixation and retrieval device includes a bone plate and a plurality of screws. The bone plate has a plurality of slot holes via which the screws are fastened onto vertebrae under treatment. The screws have a head, a neck, and a threaded stem in sequence. At least one of the slot holes of the bone plate is a long slot hole having a dimension so that the neck of the screw is restricted in the lateral direction and is able to move in the longitudinal direction of the long slot hole.

9 Claims, 6 Drawing Sheets

SPINAL FIXATION AND RETRIEVAL DEVICE

FIELD OF THE INVENTION

The present invention relates generally to a spinal fixation and retrieval device, and more particularly to a spinal fixation and retrieval device capable of providing micromotion.

BACKGROUND OF THE INVENTION

The conventional spinal fixation and retrieval device contains a rigid bone plate and bone nails, which is implanted in the body of a patient under spinal treatment with the bone nails and the bone plate being intimately joined together. In light of the intervertebral distance being caused to shorten by the body weight of the patient in the wake of surgery, the bone plate and bone nails are susceptible to falling apart. The bone nails are even vulnerable to severance. In addition, all the bone nails fastened onto the bone plate are prone to be affected, when one bone nail is out of order. As shown in FIGS. 1a, and 1b, the prior art device comprises a bone plate 100' and a plurality of screws 200'. FIG. 1a shows a schematic view taken immediately after the surgery. FIG. 1b is a side view of FIG. 1a. The prior art device is implanted into the spinal segments 600 and 650. The letter "D" denotes the distance between the two spinal segments 600 and 650. Immediately after the surgery, the bone nails 200', the spinal segments 600 and 650, and the bone plate 100' are intimately joined together such that the threaded stems 280 are parallel to each other. FIGS. 1c and 1d are schematic views taken in a period after the surgery. As shown in FIG. 1c, the distance "d" becomes smaller, due to the body eight of the patient. As shown in FIG. 1d, the threaded stems 280 are no longer parallel to each other; they form therebetween an acute angle. As a result, the bone nails 200' are apt to become unfastened. A crack or severance may occur in the necks 220' of the bone nails 200'.

With a view to providing a solution to the problem described above, this inventor of the present invention disclosed a drawer-type vertebral auxiliary fixation device capable of providing micromotion in U.S. Pat. No. 5,616,142. However, this drawer-type device is by no means free of deficiency. For example, the drawer-type device can not be easily bent to conform to the spinal curvature. In addition, the structural strength of the drawer-type device is often inadequate unless the device has an appropriate height. Moreover, the drawer-type device does not have a supporting force at the time when the surgery is completed.

SUMMARY OF THE INVENTION

It is therefore the primary objective of the present invention to provide a spinal fixation and retrieval device which is free of the drawbacks of the prior art devices described above.

In keeping with the principle of the present invention, the foregoing objective of the present invention is attained by the spinal fixation and retrieval device comprising:

a bone plate having a plurality of slot holes; and a plurality of screws, said screws being fastened via said slot holes onto vertebrae under treatment, at least one of which has a head, a threaded stem, and a neck connecting said head and said threaded stem;

wherein at least one of said plurality of slot holes is a long slot hole provided with a protruded edge at a bottom of each of two opposite walls defining a width thereof; wherein said head has a diameter ranging between said width of said long slot hole and a distance between said protruded edges.

Preferably, said long slot hole is slanted outward from said bottom to an upper portion thereof.

Preferably, said neck has a diameter smaller than said distance between said protruded edges.

Preferably, said threaded stem comprise a first spiral ridge adjacent to said neck having a diameter greater than said distance between said protruded edges and a shank next to said first spiral ridge having a diameter smaller than said distance between said protruded edges. More preferably, said first spiral ridge has the greatest diameter in said threaded stem.

Preferably, said protruded edges has a thickness substantially smaller than a pitch between said first spiral ridge and a second spiral ridge next to said first spiral ridge.

The present invention also provides a spinal fixation and retrieval device comprising:

a bone plate having a plurality of slot holes; and a plurality of screws, said screws being fastened via said slot holes onto vertebrae, at least one of which has a head, a threaded stem, and a neck connecting said head and said threaded stem;

wherein at least one of said slot holes is a long slot hole having two opposite walls defining a width of said long slot hole, and said two opposite walls further being slanted outward from a bottom portion to an upper portion thereof; wherein said head has a diameter ranging between a relatively longer distance between said upper portions and a relatively shorter distance between said bottom portions of said two opposite walls.

Preferably, said neck has a diameter smaller than said relatively shorter distance between said bottom portion of said two opposite walls.

Preferably, said threaded stem comprise a first spiral ridge adjacent to said neck having a diameter greater than said relatively shorter distance between said bottom portions of said two opposite walls and a shank next to said first spiral ridge having a diameter smaller than said relatively shorter distance between said bottom portions of said two opposite walls. More preferably, said bottom portions of said two opposite walls have a thickness substantially smaller than a pitch between said first spiral ridge and a second spiral ridge next to said first spiral ridge.

DETAILED DESCRIPTION OF THE EMBODIMENTS

Figure 3:
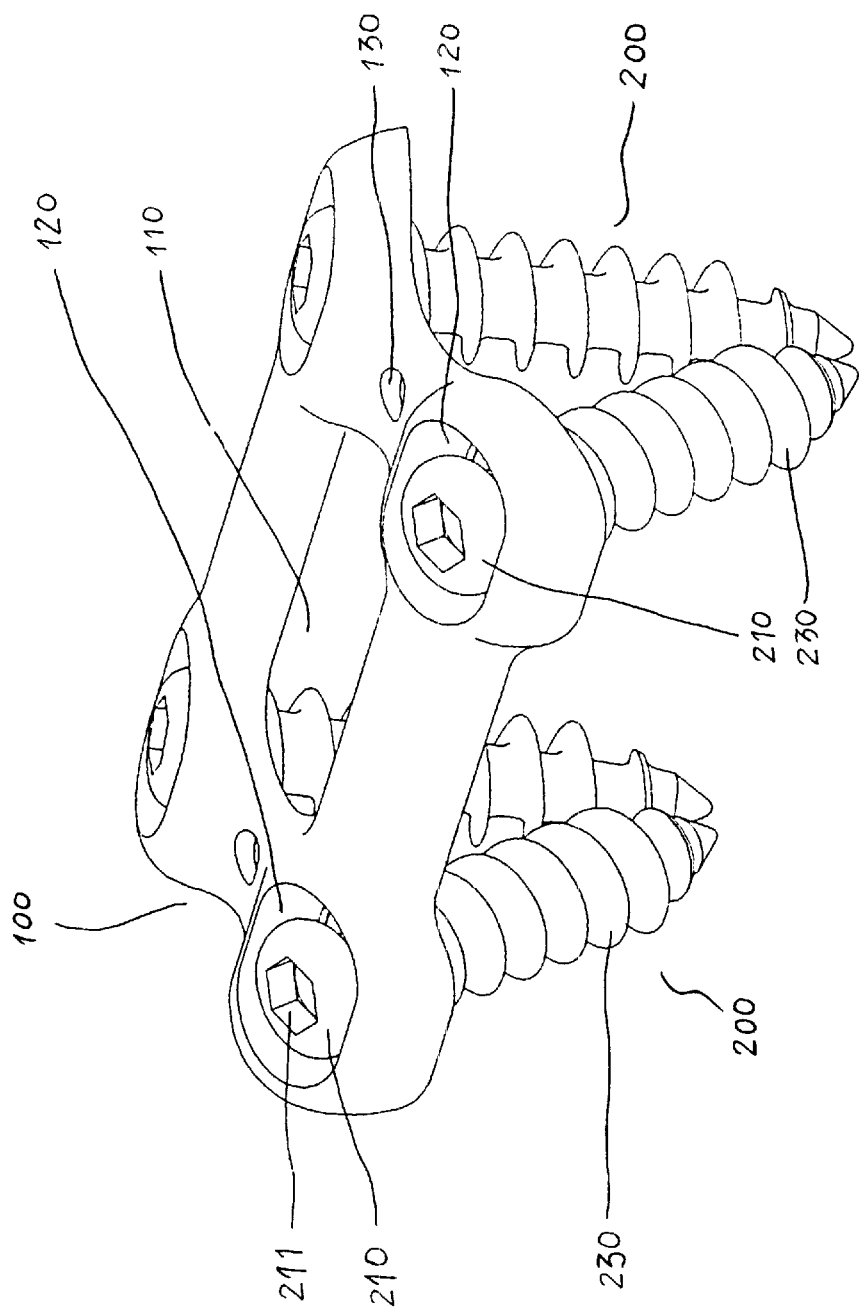
FIG. 3 show a schematic perspective view of the spinal fixation and retrieval device of the first embodiment of the present invention.
Figure 4B:
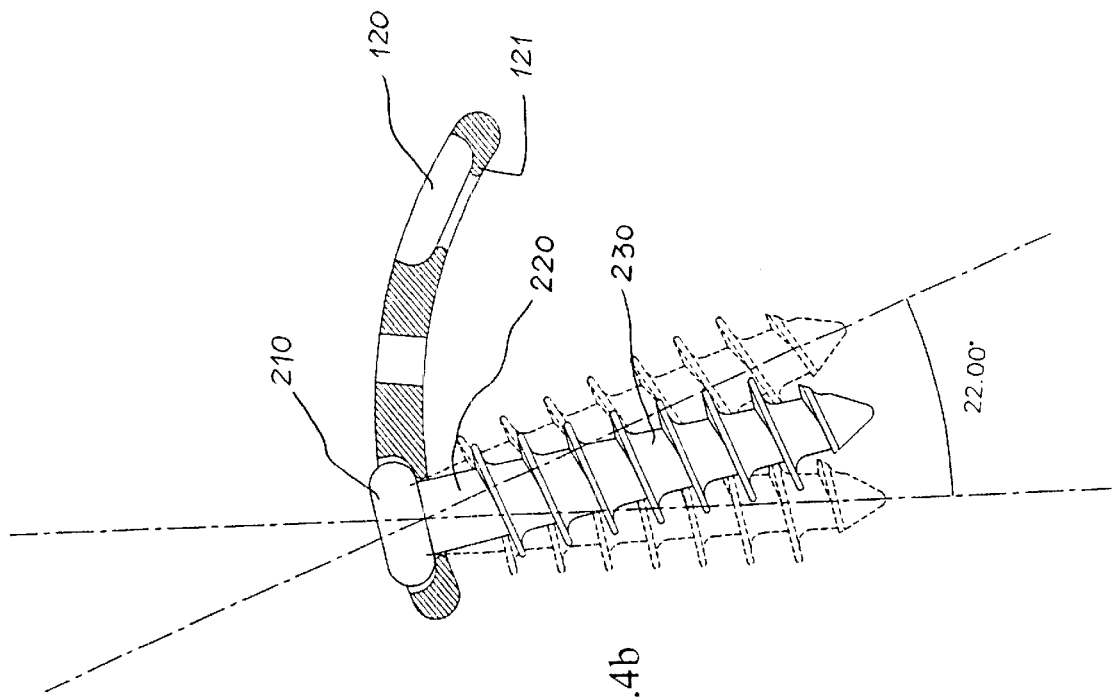
FIGS. 4a and 4b are partial lateral cross-sectional view of the spinal fixation and retrieval device of the first embodiment of the present invention.
Figure 4A:
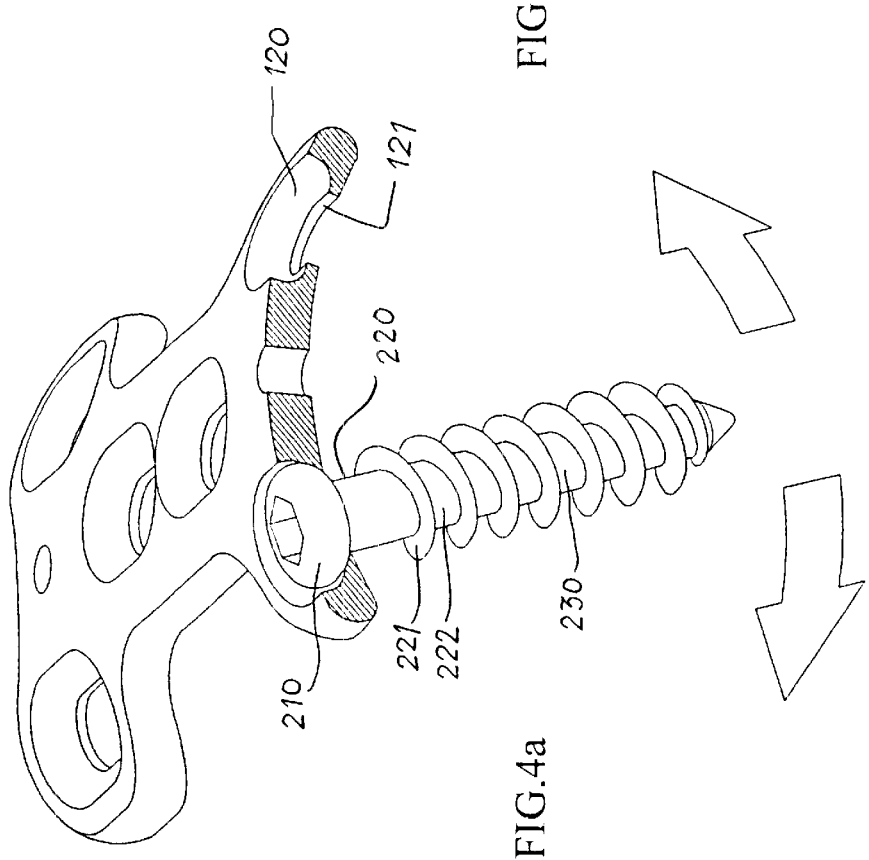
Figure 5:
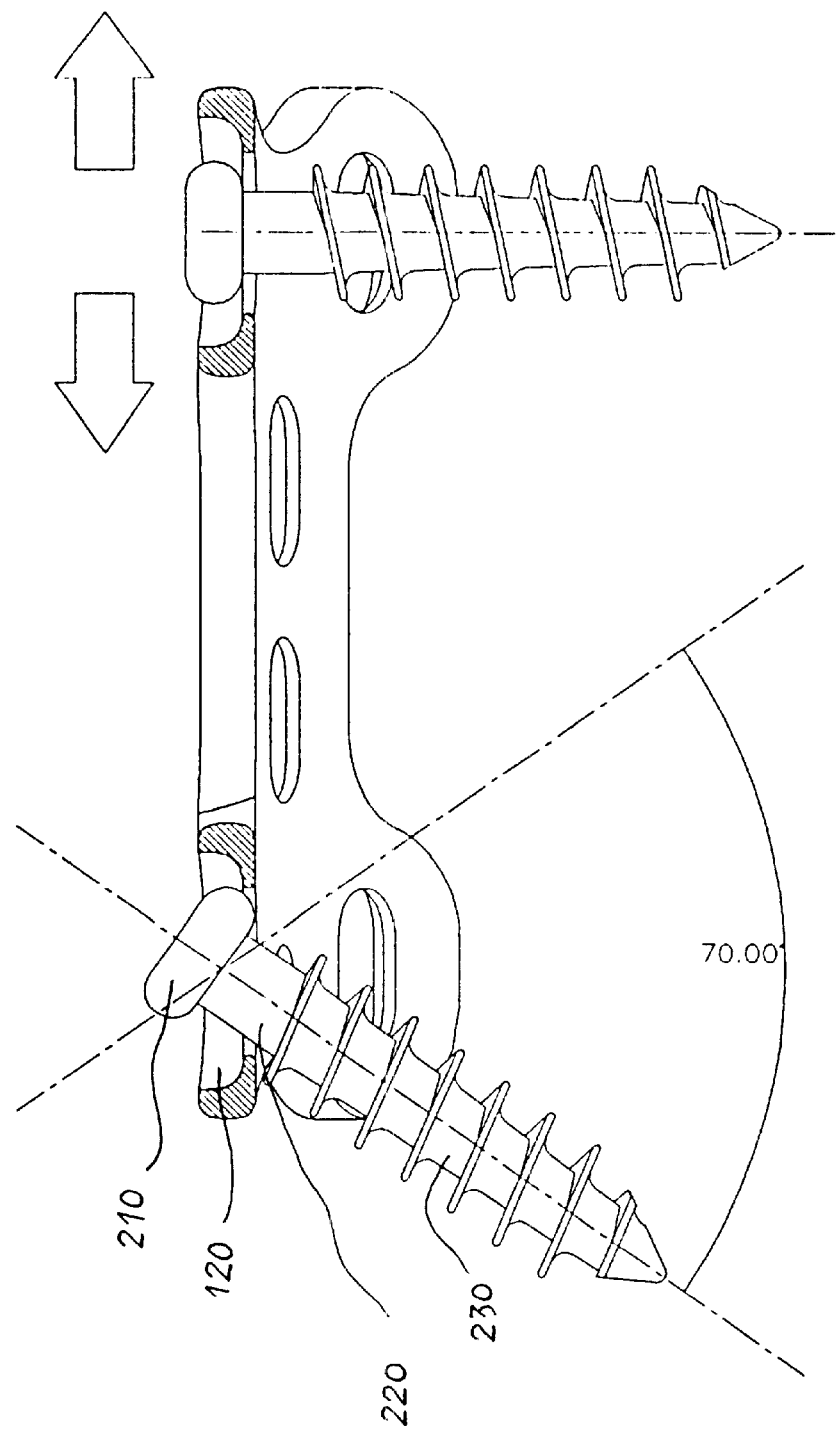
FIG. 5 is a partial longitudinal cross-sectional view of the spinal fixation and retrieval device of the first embodiment of the present invention.

As shown in FIGS. 3 to 5, the spinal fixation and retrieval device constructed according to a first embodiment of the present invention comprises a bone plate 100 and a plurality of screws 200.

The bone plate 100 is provided with a plurality of slot holes 120, via which the screws 200 are fastened onto spinal segments under treatment. The screws have a head 210, a neck 220, and a threaded stem 230.

The slot holes 120 are long slot holes, each of which is provided at the bottom with a protruded edge 121. The head 210 of the screw has a diameter ranging between the short diameter of the long slot hole 120 and the short diameter of the protruded edge 121, and the neck 220 has a diameter is slightly smaller than the short diameter of the protruded edge 121. The diameter of the head 210 of the screw is smaller than the long diameter of the long slot hole 120. Therefore, the screws 200 will be restricted in the lateral direction of the long slot hole 120 after the plate 100 and the screws 200 are implanted onto the vertebrae, but the screws 200 and the plate 100 are able to move relatively in the longitudinal direction of the long slot hole 120.

Figure 6:
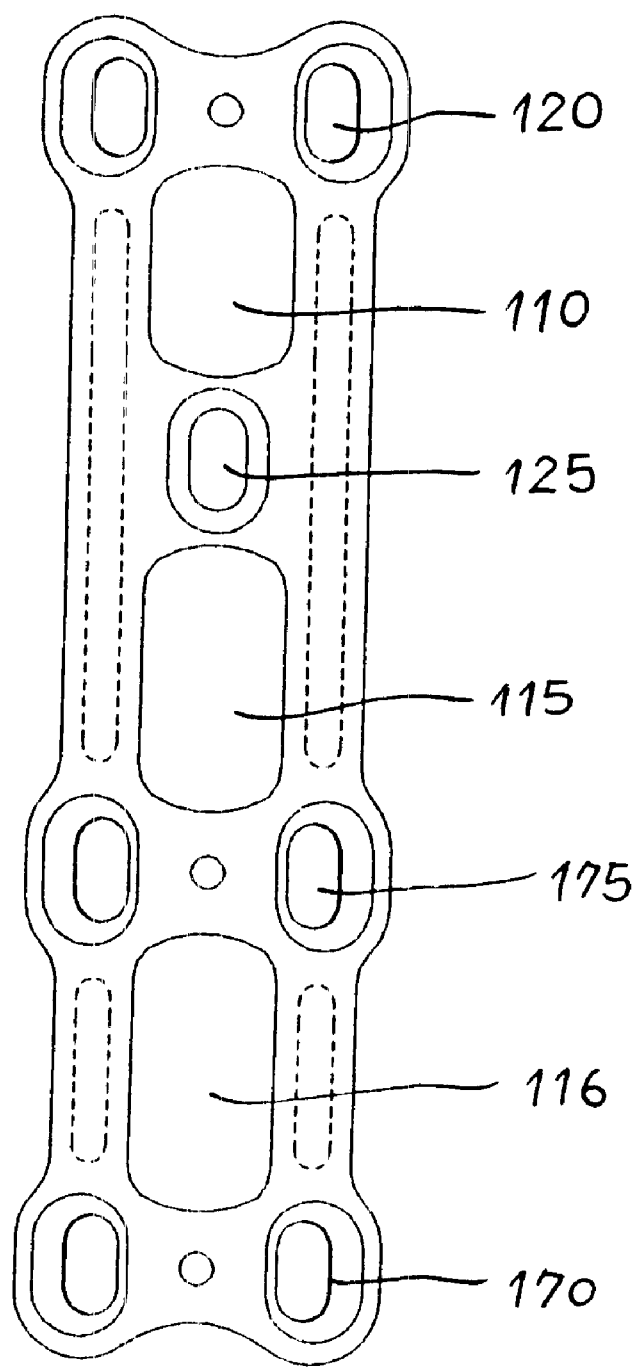
FIG. 6 show a top view of the spinal fixation and retrieval device according to a second embodiment of the present invention.

The bone plate 100 of the present invention is similar in shape and structure to the prior art bone plates; however, at least one of the holes of the bone plate of the present invention is a long slot hole 120 having a long diameter and a short diameter due to its elongated shape as illustrated in FIGS. 4a and 5 and especially in FIG. 6. As can be seen is these figures long slot holes 120 are longer in a longitudinal direction (i.e., the long diameter) than in the lateral direction (i.e., the short diameter). In other words long slot holes 120 have a longitudinal length which is greater than the lateral width. Instead of the protruded edge 121 provided at the bottom of the long slot hole 120, the long slot hole 120 may be provided with slanted outward from the bottom to the upper portion of the bone plate. In this case, the long diameter and the short diameter of the upper portion of the long slot hole are respectively greater than the long diameter and the short diameter of the bottom of the long slot hole. The word "upper" refers to a face away from the post-surgery spinal segment. The word "bottom" refers to a face toward the post-surgery spinal segment. The definitions of "upper" and "lower" are applicable throughout the entire text of this specification.

The holes of the bone plate may be provided in a manner so that only one hole is used per spinal segment. According to the present invention, as least one of the holes is a long slot hole 120. In the event that the n number (n>2) of the spinal segments are to be fixed and only one hole is used per spinal segment, preferably n−1 number of the holes of the bone plate are long slot holes 120. If the holes of the bone plate are provided in a manner so that a pair of holes are used per spinal segment, as least one pair of the holes are long slot holes 120 according to the present invention. In the same pattern, for the bone plate fixing n (n>2) spinal segments and only one pair of holes are used per spinal segment, preferably n−1 pairs of the holes of the bone plate are long slot holes 120. Of course, all slot holes may be long slot holes as shown in the first embodiment of the present invention. The bone plate may be further provided with a center hole 110 and locating holes 130, which are located between the slot holes 120, as shown in FIG. 3. The bone plate may be further provided with one or more tool holes. The center hole, tool hole, and locating hole are optional.

The screws used in the present invention are similar in construction to the prior art screws having a head, a neck, and a threaded stem; preferably, the threaded stem has a special thread. The head 210 is of any shape, preferably, round shape. The head 210 has a diameter which is substantially smaller than the short diameter of the upper portion of the long slot hole 120 and is greater than the short diameter of the protruded edge 121 of the long slot hole 120. The head 210 may be further provided with a tool hole 211. The neck 220 has a diameter which is slightly smaller than the short diameter of the protruded edge 121 of the long slot hole. The threaded stem 230 as shown in FIG. 4a has a first spiral ridge 221 contiguous to the neck 220 and a first shank 222. Preferably, the short diameter of the protruded edge 121 of the long slot hole ranges between the diameter of the first spiral ridge 221 and the diameter of the first shank 222, thereby enabling the screw 200 to be better equipped to join with the bone plate 100. The protruded edge 121 has a thickness, which is smaller than the pitch of the thread stem 230. Preferably, the thickness of the protruded edge 121 is substantially about equal to the pitch of the threaded stem 230. The threaded stem 230 of the screw 200 is gradually smaller in diameter from the first spiral ridge 221, and may be equal in diameter.

Figures 1A, 1B, 1C, 1D:
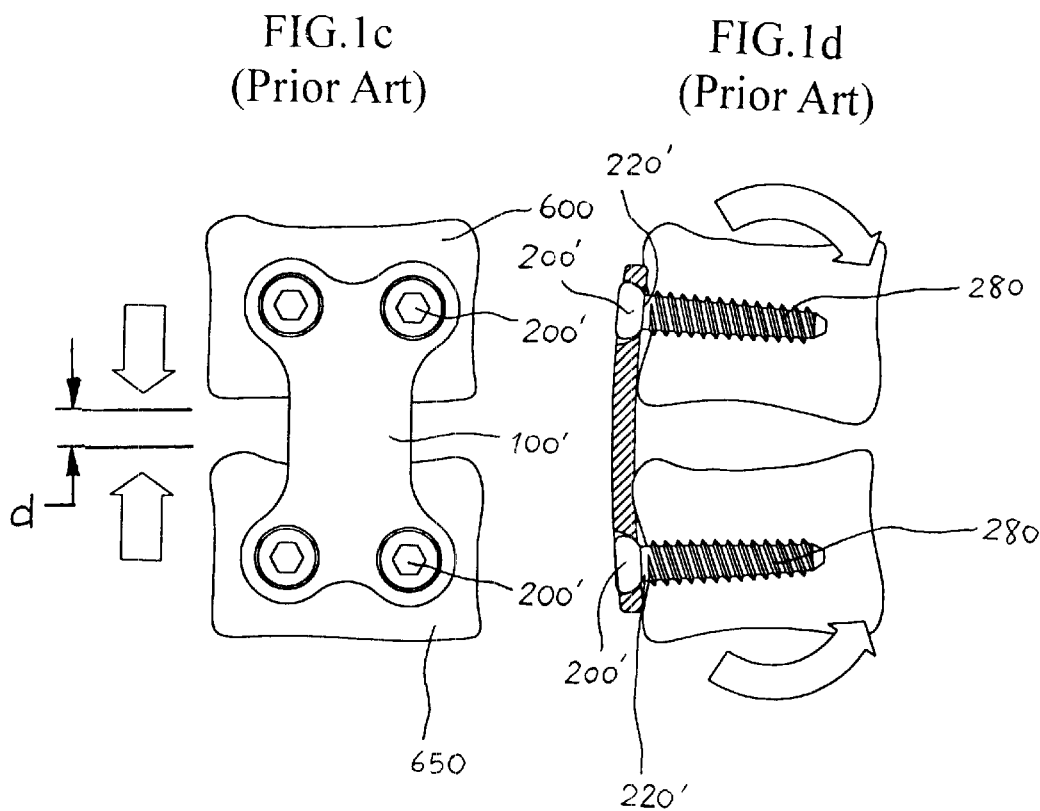
FIGS. 1a and 1b show a top view and a cross-sectional view of the prior art spinal fixation and retrieval device at the time when the surgery is completed.
FIGS. 1c and 1d show a top view and a cross-sectional view of the prior art spinal fixation and retrieval device after the surgery.
Figures 2A, 2B:
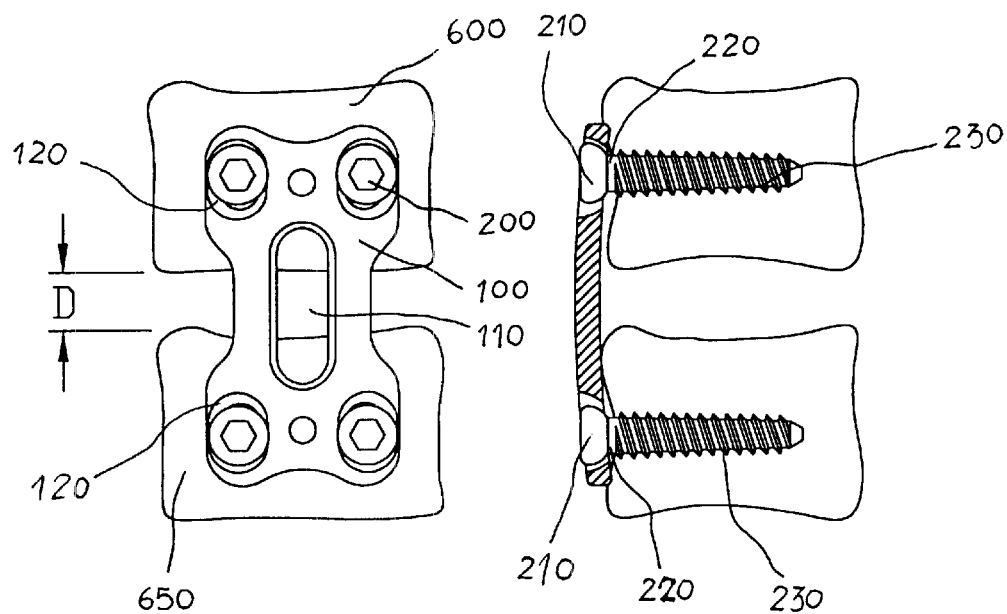
FIGS. 2a and 2b show a top view and a cross-sectional view of the spinal fixation and retrieval device according to a first embodiment of the present invention at the time when the surgery is completed.
Figures 2C, 2D:
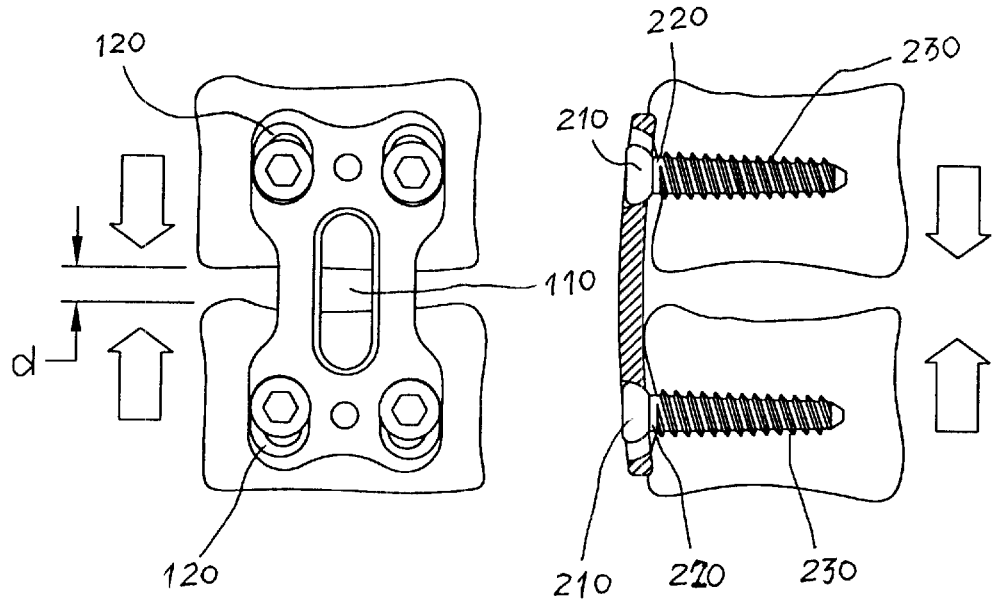
FIGS. 2c and 2d show a top view and a cross-sectional view of the spinal fixation and retrieval device of the first embodiment of the present invention after the surgery is completed.

The device of the present invention is implanted into the spinal segments 600 and 650, as shown in FIGS. 2a and 2b. The letter "D" denotes the distance between the two spinal segments 600 and 650. Immediately after the surgery, the screws 200, the spinal segments 600 and 650, and the bone plate 100 are intimately joined together such that the threaded stems 230 are parallel to each other. As shown in FIGS. 2c and 2d, in a period after the surgery, the distance between the spinal segments 600 and 650 "d" becomes smaller because of the pressure of body weight or other factors. Accordingly, the screws 200 are caused to displace in the slot holes 120 and move inward. The word "inward" refers to the direction toward the center of the bone plate 100.

FIGS. 4a and 4b show that the device of the present invention can be implanted at various angles in the lateral direction, with the maximum angle being 22 degrees. The allowable angle can be much greater by a design change in the protruded edge 121 and the head 210 of the screws 200. The bone plate shown in FIGS. 4a and 4b is provided with two center holes.

FIG. 5 is similar to FIG. 4b, but in the longitudinal direction. The screw 200 can be fastened onto the spinal segment via the long slot hole at various angles in the longitudinal direction, with the maximum angle being 70 degrees. The bone plate shown in FIG. 5 is provided with two center holes.

The spinal fixation and retrieval device according to a second embodiment of the present invention is shown in FIG. 6, wherein the reference numerals of 110, 115, and 116 denote the center holes, whereas the reference numerals of 120, 125, 170, and 175 denote the long slot holes. The bone plate is intended for use in fixing four spinal segments. The bone plate can be easily bent to conform to the curvatures of the four spinal segments, thanks to the center holes 110, 115, and 116.

What is claimed is:

1. A spinal fixation and retrieval device comprising:
a bone plate having a plurality of slot holes; and
a plurality of screws, said screws being screwed via said slot holes directly into vertebrae under treatment, at least one of which has a head, a threaded stem, and a neck connecting said head and said threaded stem;
wherein at least one of said plurality of slot holes is a long slot hole provided with a protruded edge at a bottom of each of two opposite walls defining a lateral width of said long slot; wherein said head has a diameter ranging between said width of said long slot hole and a distance between said protruded edges; and said long slot hole has a longitudinal length which is greater than said lateral width; and said threaded stem comprises a first spiral ridge adjacent to said neck having a diameter greater than said distance between said protruded edges and a shank next to said first spiral ridge having a diameter smaller than said distance between said protruded edges; and said protruded edges has a thickness substantially smaller than a pitch between said first spiral ridge and a second spiral ridge next to said first spiral ridge.

2. The device as defined in claim 1, wherein said long slot hole is slanted outward from said bottom to an upper portion thereof.

3. The device as defined in claim 1, wherein said neck has a diameter smaller than said distance between said protruded edges.

4. The device as defined in claim 1, wherein said first spiral ridge has the greatest diameter in said threaded stem.

5. A spinal fixation and retrieval device comprising:
a bone plate having a plurality of slot holes; and
a plurality of screws, said screws being screwed via said slot holes directly into vertebrae, at least one of which has a head, a threaded stem, and a neck connecting said head and said threaded stem;
wherein at least one of said slot holes is a long slot hole having two opposite walls defining a lateral width of said long slot hole, and said two opposite walls further being slanted outward from a bottom portion to an upper portion thereof; wherein said head has a diameter ranging between a relatively longer distance between said upper portions and a relatively shorter distance between said bottom portions of said two opposite walls; and said long slot hole has a longitudinal length which is greater than said lateral width; and said threaded stem comprises a first spiral ridge adjacent to said neck having a diameter greater than said relatively shorter distance between said bottom portions of said two opposite walls and a shank next to said first spiral ridge having a diameter smaller than said relatively shorter distance between said bottom portions of said two opposite walls.

6. The device as defined in claim 5, wherein said neck has a diameter smaller than said relatively shorter distance between said bottom portions of said two opposite walls.

7. The device as claimed in claim 6, wherein said bottom portions of said two opposite walls have a thickness substantially smaller than a pitch between said first spiral ridge and a second spiral ridge next to said first spiral ridge.

8. A method for implanting a spinal fixation and retrieval device onto vertebrae, wherein said spinal fixation and retrieval device comprises:
a bone plate having a plurality of slot holes; and
a plurality of screws, said screws being fastened via said slot holes onto vertebrae under treatment, at least one of which has a head, a threaded stem, and a neck connecting said head and said threaded stem;
wherein at least one of said plurality of slot holes is a long slot hole provided with a protruded edge at a bottom of each of two opposite walls defining a lateral width of said long slot; wherein said head has a diameter ranging between said width of said long slot hole and a distance between said protruded edges; and said long slot hole has a longitudinal length which is greater than said lateral width:
said method comprising fastening said plurality of screws via said at least one long slot hole onto vertebrae so that a longitudinal direction of said at least one long slot hole is substantially parallel to a longitudinal direction of a spine containing said vertebrae whereby movement of said vertebrae toward one another causes said head of the screw to move longitudinally in said long slot, thereby permitting micromotion between the vertebrae connected by said device after implantation.

9. A method for implanting a spinal fixation and retrieval device onto vertebrae, wherein said spinal fixation and retrieval device comprises
a bone plate having a plurality of slot holes; and
a plurality of screws, said screws being fastened via said slot holes onto vertebrae, at least one of which has a head, a threaded stem, and a neck connecting said head and said threaded stem;
wherein at least one of said slot holes is a long slot hole having two opposite walls defining a lateral width of said long slot hole, and said two opposite walls further being slanted outward from a bottom portion to an upper portion thereof; wherein said head has a diameter ranging between a relatively longer distance between said upper portions and a relatively shorter distance between said bottom portions of said two opposite walls; and said long slot hole has a longitudinal length which is greater than said lateral width:
said method comprising fasting said plurality of screws via said at least one long slot hole onto vertebrae so that a longitudinal direction of said at least one long slot hole is substantially parallel to a longitudinal direction of a spine containing said vertebrae whereby movement of said vertebrae toward one another causes said head of the screw to move longitudinally in said long slot, thereby permitting micromotion between the vertebrae connected by said device after implantation.

* * * * *